(12) United States Patent
Burcin et al.

(10) Patent No.: US 10,155,927 B2
(45) Date of Patent: Dec. 18, 2018

(54) METHOD FOR DIFFERENTIATION OF PLURIPOTENT STEM CELLS INTO CARDIOMYOCYTES

(71) Applicant: Hoffmann-La Roche Inc., Little Falls, NJ (US)

(72) Inventors: Mark Burcin, Basel (CH); Sonja Schlicht, Riehen (CH)

(73) Assignee: HOFFMANN-LA-ROCHE INC., Little Falls, NJ (US)

( * ) Notice: Subject to any disclaimer, the term of this patent is extended or adjusted under 35 U.S.C. 154(b) by 0 days.

(21) Appl. No.: 14/705,656

(22) Filed: May 6, 2015

(65) Prior Publication Data

US 2015/0353893 A1 Dec. 10, 2015

(30) Foreign Application Priority Data

May 6, 2014 (EP) .................................... 14167201

(51) Int. Cl.
*C12N 5/00* (2006.01)
*C12N 5/077* (2010.01)

(52) U.S. Cl.
CPC ........ *C12N 5/0657* (2013.01); *C12N 2500/38* (2013.01); *C12N 2501/415* (2013.01); *C12N 2501/727* (2013.01); *C12N 2501/999* (2013.01); *C12N 2503/00* (2013.01); *C12N 2506/02* (2013.01); *C12N 2506/45* (2013.01)

(58) Field of Classification Search
CPC .............. C12N 5/0657; C12N 2506/45; C12N 2506/02
See application file for complete search history.

(56) References Cited

U.S. PATENT DOCUMENTS

2012/0225480 A1* 9/2012 Amit .................... C12N 5/0606 435/366

FOREIGN PATENT DOCUMENTS

| WO | WO 2010/101849 | * | 9/2010 | ........... C07D 213/75 |
| WO | 2012/168167 A1 | | 12/2012 | |
| WO | 2013/056072 A1 | | 4/2013 | |

OTHER PUBLICATIONS

Lian et al. PNAS. www.pnas.org/cgl/doi/10.1073/pnas. 1200250109: E1848-E1857, May 29, 2012.*
International Search Report and Written Opinion for PCT/EP2015/059745 ( Jul. 20, 2015).
Lian et al., "Directed cardiomyocyte differentiation from human pluripotent stem cells by modulating Wnt/β-catenin signaling under fully defined conditions" Nature Protocols 8(1 SUPPL 162-175) ( 2013).
Zhang et al., "Tissue-engineered cardiac patch for advanced functional maturation of human ESC-derived cardiomyocytes" Biomaterials 34:5813-5820 ( 2013).

* cited by examiner

*Primary Examiner* — Marcia S Noble
(74) *Attorney, Agent, or Firm* — Steven Cui

(57) ABSTRACT

This application relates to a method for differentiating pluripotent stem cells (PSCs) into cardiomyocytes. Moreover this application relates to a method for differentiating human embryonic stem cells (hESCs) and induced pluripotent stem cells (iPSCs) into defined cardiomyocytes based on linked steps of chemically defined medium inductions.

7 Claims, 6 Drawing Sheets

METHOD FOR DIFFERENTIATION OF PLURIPOTENT STEM CELLS INTO CARDIOMYOCYTES

RELATED APPLICATIONS

Figure 1:
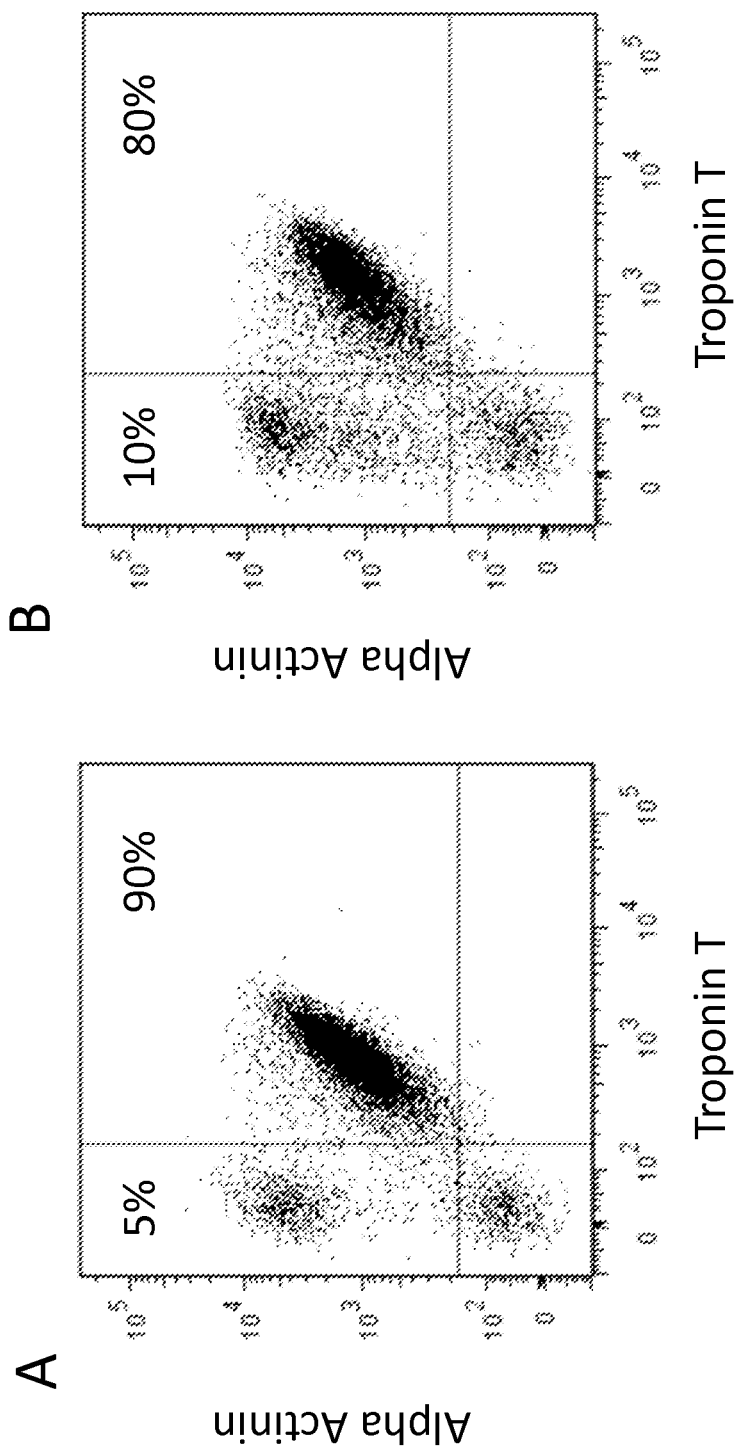

This application claims the benefit of European Patent Application No. EP 14167201.4, filed on 6 May 2014, which is incorporated by reference herein in its entirety.

FIELD OF THE INVENTION

This application relates to a method for differentiating pluripotent stem cells (PSCs) into cardiomyocytes. Moreover this application relates to a method for differentiating human embryonic stem cells (hESCs) and induced pluripotent stem cells (iPSCs) into proliferating cardiomyocytes based on linked steps of chemically-defined medium inductions.

BACKGROUND

For many years, various cell culture systems have been used in preclinical drug development. However, established cell models only partially reflect pharmaceutically relevant disease-specific physiology because they are either derived from tumorigenic tissue or from transformed and immortalized cells. In particular, because terminally-differentiated cardiomyocytes have been shown to possess limited proliferative potential, they do not have the capacity to effectively generate cell models for drug development. Hence there is a need for more disease relevant human cell types that can be used as reliable cell models in research and drug development.

Human embryonic stem cells (hESC) and induced pluripotent stem cells (iPSC) provide researchers with immense opportunities for generating functional human cell types such as cardiomyocytes, neuronal cells, pancreatic cells, etc. Robust protocols for in vitro differentiation of pure hESC- and iPSC-derived human cardiomyocyte (hESCM) cultures would present a powerful tool, not only to advance the understanding of early human cardiogenesis, but also to use the cardiomyocytes as a non-transformed human cell model to test drug efficacy in preclinical stages of drug development and to assess cardiac toxicity before entering the clinic. Additionally, hESC-derived human cardiomyocytes could open opportunities for identifying pathways critical to cardiac regeneration and ultimately lead to clinical applications supporting stem-cell based therapy.

For developing cell assay models for pharmaceutical research and development, such differential protocols need to generate cells that ideally fulfill the following criteria: a) are robust with a high level of reproducibility; b) generate large numbers of highly pure cell types; c) can be differentiated in a short time; d) generate cells that can be frozen to ensure batch conformity for multiple screening campaigns; e) provide functionality and physiology relevant for modeling disease-specific readouts. (For a review of prior art approaches to differentiate pluripotent cells into cardiomyocytes, see Burridge et al. (2012) Cell Stem Cell 10:16-28.) So far none of the known protocols fulfil the criteria above. In particular, cardiomyocytes obtained through the known protocols are difficult to freeze and thaw without losing any functional properties.

To fulfill these requirements, the instant inventors developed a novel differentiation method that generates large numbers of highly pure cardiomyocytes (up-to 95%). The differentiation protocol makes use of defined small molecules to direct differentiation towards the cardiac lineage in a time span of 10 days. To further increase their purity, the cardiomyocytes are enriched by replating them using conditions that are preferential for cardiomyocytes. Furthermore, the cardiomyocytes can afterwards be frozen, stored under liquid nitrogen, and thawed again. The cardiomyocytes have been tested to be compliant with several screening formats used in pharmaceutical research and development. The present invention provides an improved method for differentiating pluripotent stem cells into cardiomyocytes in a shorter amount of time and with a significantly increased yield compared to prior art protocols. The new method alleviates the necessity of obtaining embryoid bodies or small cell clumps from pluripotent stem cells and removes the major drawback of low reproducibility and standardization of methods known so far. Moreover, the high efficiency allows the use of these defined cardiomyocytes in large scales in drug discovery and safety assessments, in regenerative medicine applications, and in in vitro disease modeling in the pharmaceutical industry.

SUMMARY OF THE INVENTION

Provided herein is a method for differentiating pluripotent stem cells into cardiomyocytes, said method comprising the steps of: a) providing pluripotent cells at a density of $3\text{-}7\times10^5/cm^2$, and b) incubating said cells in an insulin-free medium comprising a compound of formula:

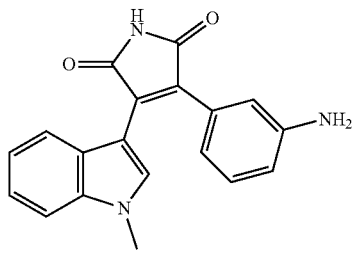 [SMILES: Cn1cc(C2=C(c3cccc(N)c3)C(=O)NC2=O)c2ccccc21]

In one embodiment, the cells are incubated in an insulin-free medium comprising 0.3-10 µM of the compound.

In one embodiment, step b) comprises incubating the cells for 12-48 hours.

In one embodiment, the method additionally comprises step c) incubating the cells in an insulin-free medium comprising Wnt-C59.

In one embodiment, step c) comprises incubating the cells in an insulin-free medium comprising 1-10 µM Wnt-C59.

In one embodiment, step c) comprises incubating the cells for 24-72 hours.

In one embodiment, the cells are incubated for 24-48 hours in insulin-free medium in between the steps.

In one embodiment, the method additionally comprises step d) incubating said cells in a medium comprising insulin.

In one embodiment, the medium of step b), c) and d) comprises ascorbic acid.

In one embodiment, the pluripotent stem cell is an induced pluripotent stem cell.

In one embodiment, the induced pluripotent stem cell is a human cell.

In one embodiment, the induced pluripotent stem cell is obtained from a subject suffering from a disease caused by dysfunction of heart cells.

In one embodiment, cardiomyocytes obtained by the method according to any one of the above embodiments are provided.

In one embodiment, a biobank of cardiomyocytes obtained by the method according to any one of the above embodiments are provided.

In one embodiment, the cardiomyocytes obtained by the method according to any one of the above embodiments or of the biobank of cardiomyocytes are used as an in vitro model for diseases caused by dysfunction of heart cells.

In one embodiment, a therapeutic composition comprising cardiomyocytes obtained by the method according to any one of the above embodiments or of the biobank of cardiomyocytes is provided.

Any one of the above embodiments may be present singly or in combination.

SHORT DESCRIPTION OF THE FIGURES

FIG. 1: FACS analysis identifies a high concentration of cardiomyocytes at differentiation day 14. Both hESC and iPSC produced similar results. A: Human embryonic stem cell-derived cardiomyocytes. B: Human induced pluripotent stem cell-derived cardiomyocytes.

Figure 2:
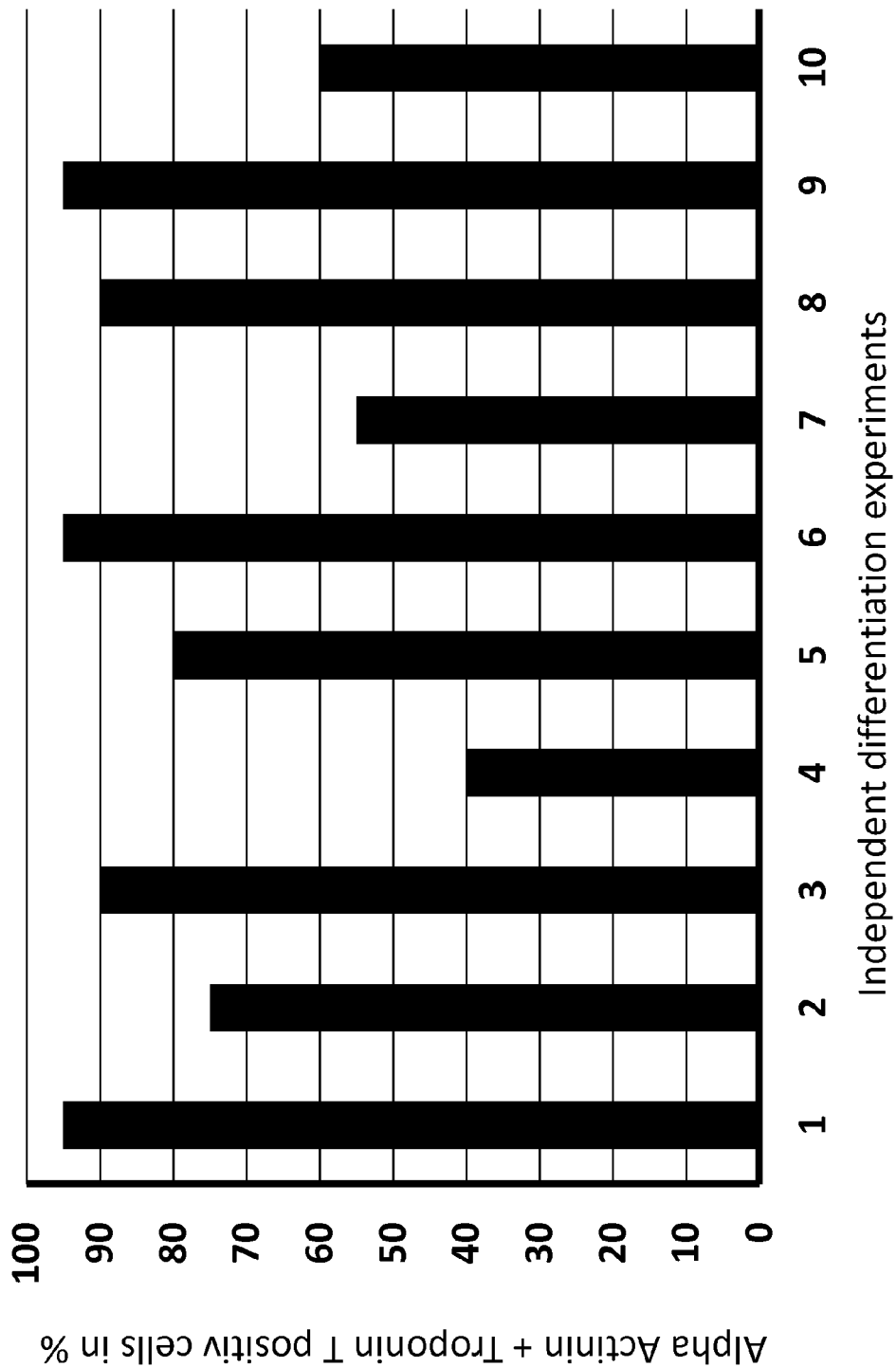

FIG. 2: FACS analysis of multiple cardiomyocyte differentiation proves robustness of the protocol.

Figure 3:
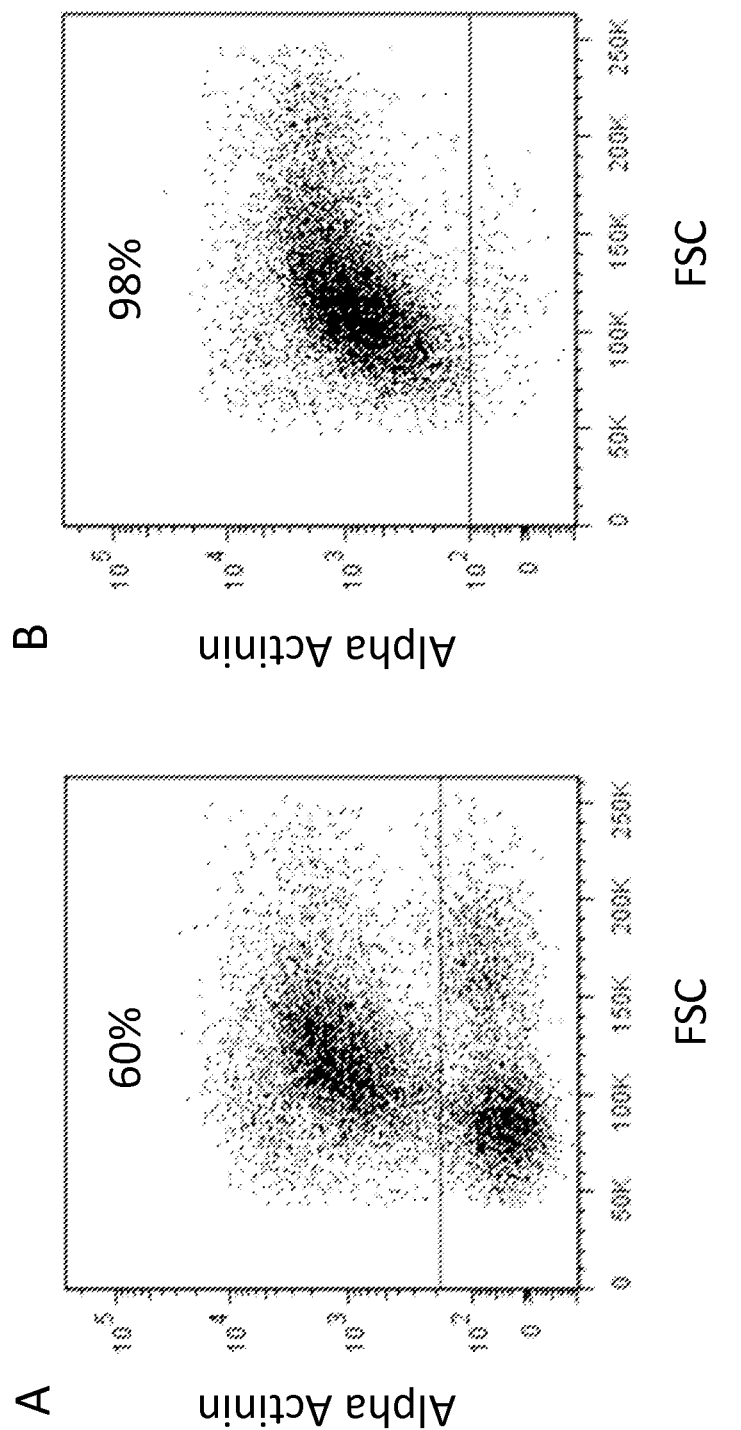

FIG. 3: FACS analysis shows that purification method improves purity of cardiomyocytes. A: 60% purity with $5.5\times10^5/cm^2$ cardiomyocytes on day 14. B: 98% purity with $4.4\times10^5/cm^2$ cardiomyocytes after additional purification step on day 21.

Figure 4:
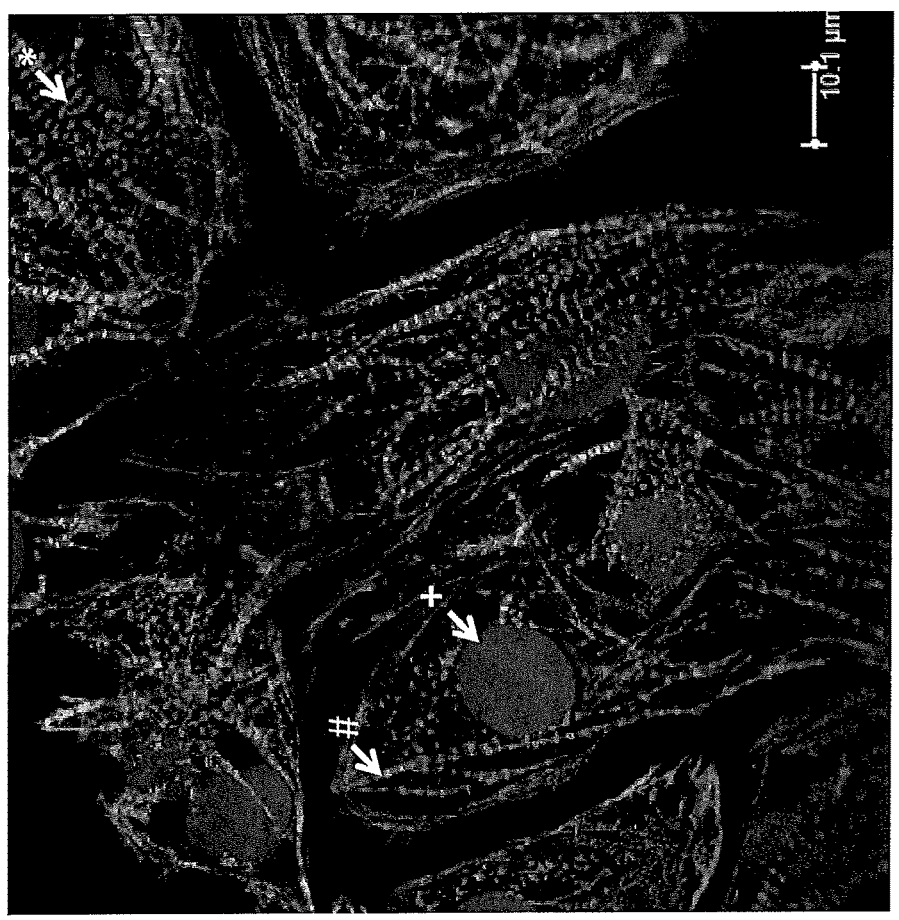

FIG. 4: Immunofluorescence staining-confocal microscope analysis reveals in cells a striation pattern by alpha actinin and troponin T that is typical for cardiomyocytes. Green (*): Alpha Actinin; Red (#): Troponin T; Blue (+): Nuclei.

Figure 5:
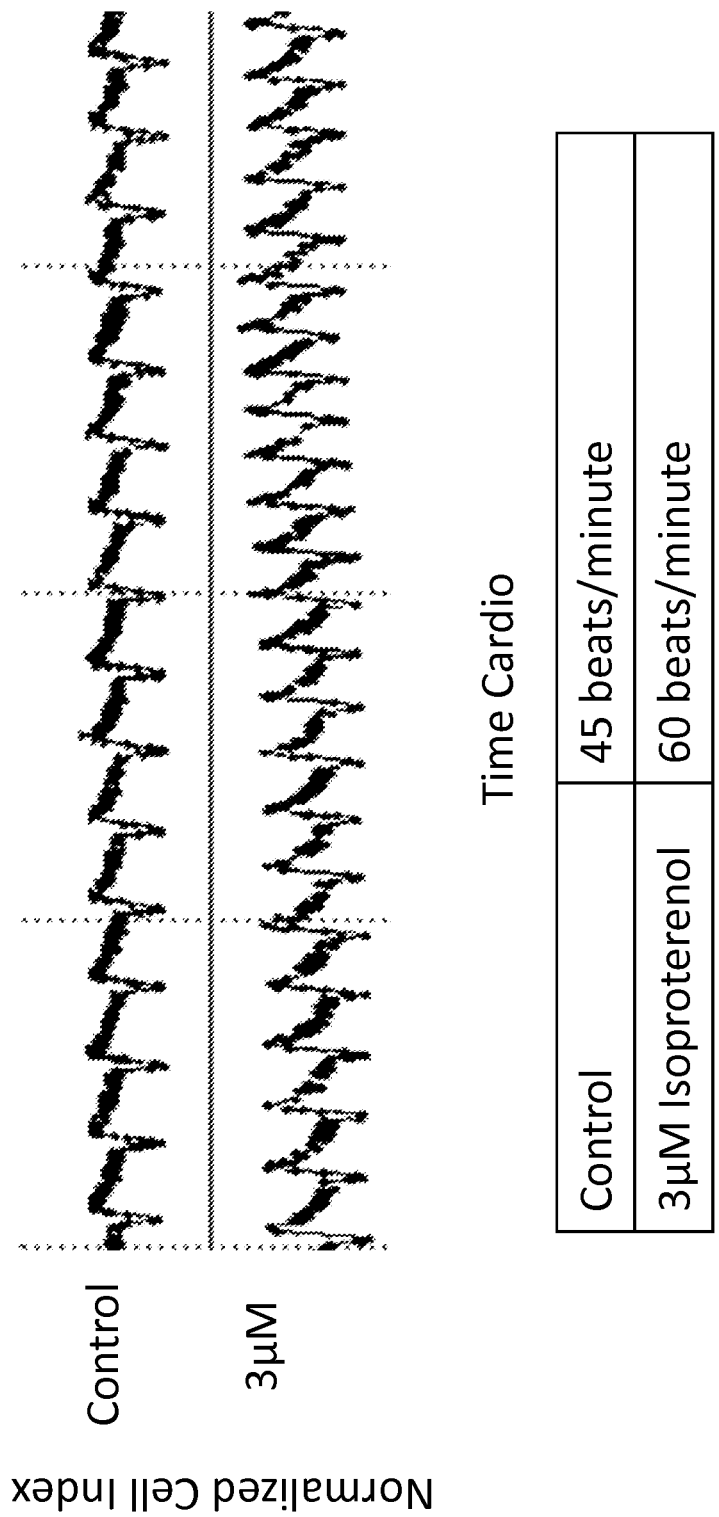

FIG. 5: xCELLigent analysis—isoproterenol increases beating frequency in pluripotent stem cell derived cardiomyocytes.

Figure 6:
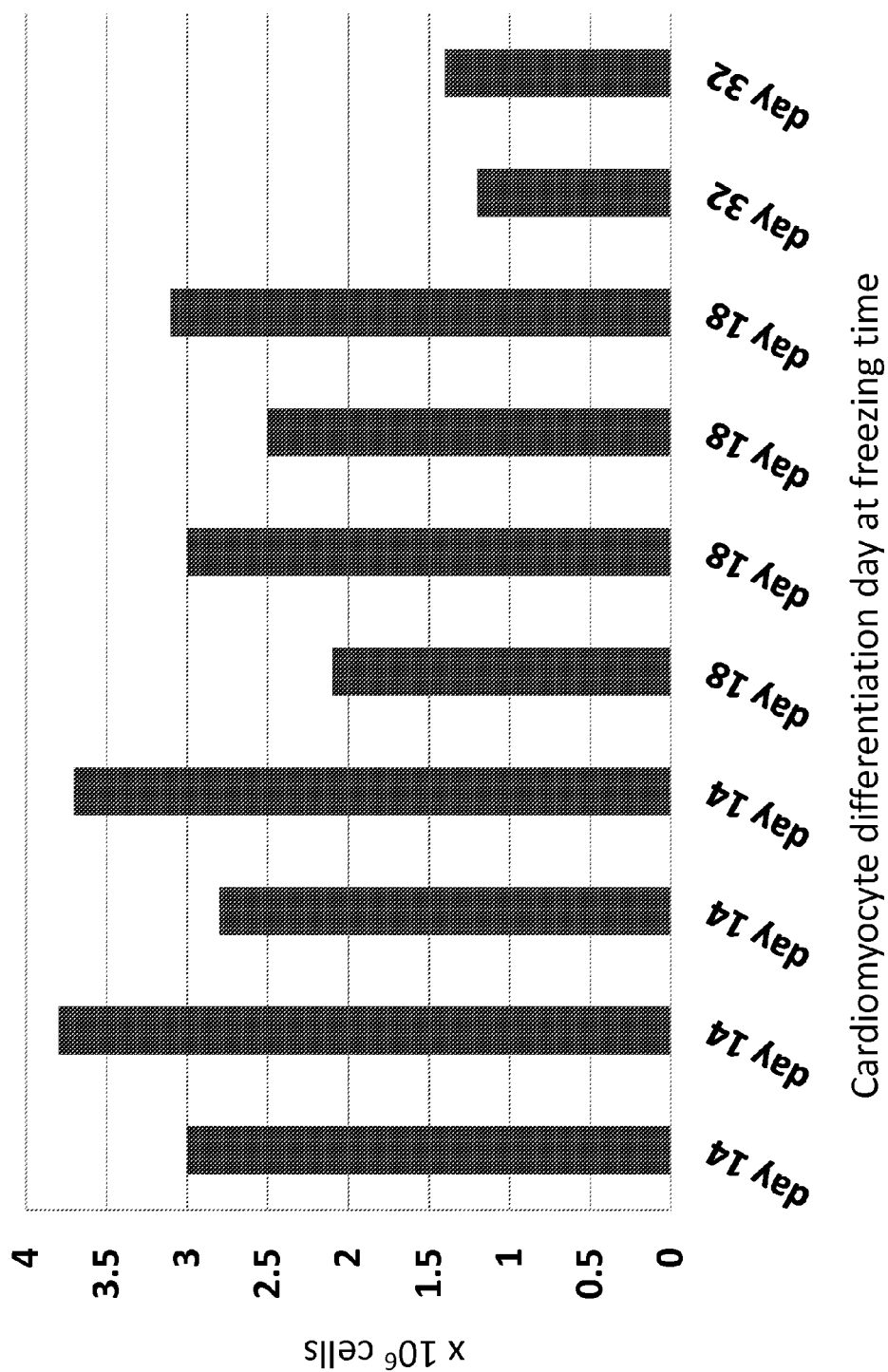

FIG. 6: Pluripotent stem cell-derived cardiomyocytes show a high rate of survival of cardiomyocyte number after thawing at differentiation day 14 and day 18. In each experiment $4\times10^6$ cells were frozen.

DETAILED DESCRIPTION OF THE INVENTION

The present invention provides an improved method for differentiating pluripotent stem cells into cardiomyocytes in a shorter amount of time and with a significantly increased yield of proliferating cardiomyocytes compared to prior art protocols.

The novel method for differentiating human embryonic stem cells (hESCs) and induced pluripotent stem cells (iPSCs) into defined cardiomyocytes disclosed herein is based on linked steps of chemically defined medium inductions, generating beating cells after only ten days (or earlier: eight days) after the differentiation was initiated.

In one embodiment a method for differentiating pluripotent stem cells into cardiomyocytes is provided, said method comprising the steps of:
  a) providing pluripotent cells at a density of $3\text{-}7\times10^5$ cells/cm$^2$, and
  b) incubating said cells in an insulin-free medium comprising a compound of formula:

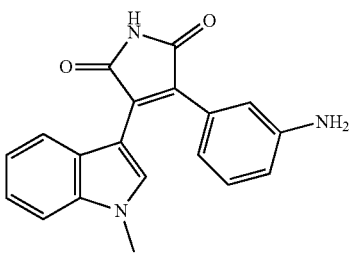 [SMILES: Cn1cc(C2=C(c3cccc(N)c3)C(=O)NC2=O)c2ccccc21]

3-(3-Amino-phenyl)-4-(1-methyl-1H-indol-3-yl)-pyrrole-2,5-dione (CP21).

The pluripotent stem cells are provided at a density of $3\text{-}7\times10^5$ cells/cm$^2$, i.e., a very high density. In one embodiment the cells are provided at a density of $5.5\times10^5$ cells/cm$^2$. Surprisingly the inventors of the present method found that providing the cells at a high density increases the differentiation efficiency and cardiomyocyte yield.

In one embodiment, the cells provided at high density are washed with a suitable buffer or medium prior to initializing differentiation with step a), to remove any dead cells.

The medium of step b) is an insulin-free medium. The lack of insulin in the early differentiation medium of step b) is important since earlier reports have shown that an insulin-containing differentiation medium blocks cardiogenesis. (See Lian et al. (2013) Stem Cells 31:447-457.)

To initialize differentiation, the cells are incubated in insulin-free medium comprising compound 21 (3-(3-Amino-phenyl)-4-(1-methyl-1H-indol-3-yl)-pyrrole-2,5-dione, also referred to as "compound 21" or "CP21" herein; see e.g., Gong et al. (2010) Bioorganic& Medicinal Chemistry Letters 20:1693-1696) to activate the wnt-pathway. The optimal concentration of compound 21 to induce cardiomyocyte differentiation is dependent on the cell density of the pluripotent cells that are attached to the cell vessel. In several parallel differentiation experiments using different cell densities ($1.8\text{-}11\times10^5$/cm2 hESC or iPSC) and various CP21 concentrations (0-10 µM), it was found that using a cell density of $5.5\times10^5$/cm$^2$ and a CP21 concentration of 2 µM resulted in the most efficient differentiation of pluripotent stem cells into cardiomyocytes. CP21 concentrations above 5 µM showed decreased cell viability. This is surprising as prior art protocols require higher concentrations of other modulators of the Wnt pathway for efficient differentiation.

In one embodiment, step b) of the differentiation method comprises incubating the cells in a medium comprising 0.3-10 µM CP21, preferably 0.5-5 µM CP21. In one preferred embodiment, step b) of the differentiation method comprises incubating the cells in a medium comprising 2 µM CP21.

After 24 h CP21 incubation, the cells show strong cell death. Testing various incubation times of CP21 showed that 24 h was optimal for cardiogenesis and longer or shorter incubation times resulted in less efficient differentiation.

In one embodiment, step b) comprises incubating the cells for 12-48 hours, preferably for 18-24 hours, in an insulin-free medium comprising CP21.

In one preferred embodiment, step b) comprises incubating the cells for 24 hours in an insulin-free medium comprising CP21.

In one embodiment, the medium of step b) comprises ascorbic acid. The addition of ascorbic acid to the basic medium has been shown to improve cardiomyocyte differentiation. (See Cao et al. (2013) Cell Research 23:1119-1132.)

Hence, in one embodiment, the medium of step b) is an insulin-free medium comprising CP21 and ascorbic acid. In one such embodiment the medium comprises 0.5-5 µM CP21 and ascorbic acid.

In one embodiment, said method further comprises step c) incubating said cells in an insulin-free medium comprising Wnt-C59.

Wnt-C59 is a small molecule that blocks the Wnt signaling pathway (WO2010101849, 2-(4-(2-methylpyridin-4-yl) phenyl)-N-(4-(pyridin-3-yl)phenyl)acetamide). Wnt-C59 is a very potent and highly selective Wnt signaling antagonist. It prevents palmitylation of Wnt proteins by Porcupine (a membrane-bound O-acyltransferase), thereby blocking Wnt protein secretion and activity.

Using different concentrations of the wnt repressor Wnt-C59 (1-10 µM) resulted in a significant increase in cardiomyocytes. The optimal concentration was identified at 2 µM. In cases where no Wnt-C59 was added, the differentiation did not result in cardiomyocytes. Concentrations of more than 5 µM Wnt-C59 showed increased cell death. In one embodiment, step c) of the differentiation method comprises incubating the cells in a medium comprising 1-10 µM Wnt-C59. In one preferred embodiment step c) of the differentiation method comprises incubating the cells in a medium comprising 2 µM Wnt-C59.

Since the Wnt pathway is highly complex, other Wnt inhibitors with a different mode of action were tested.

Anthelmintic niclosamide (Chen et al. (2009) Biochemistry 48:10267-10274) promotes Frizzled1 endocytosis, down-regulates Dishevelled-2 protein, and inhibits Wnt3A-stimulated beta-catenin stabilization and LEF/TCF reporter activity.

Pyrvinium is a potent inhibitor of Wnt signaling by binding all casein kinase 1 (CK1) family members in vitro and selectively potentiating casein kinase 1α (CK1α) kinase activity resulting in stabilization of Axin and increased β-catenin turnover (Thorne et al. (2010) Nat Chem Biol 6:829-836.).

Anthelmintic niclosamide and Pyrvinium were tested for their ability to induce cardiomyocyte differentiation. Contrary to Wnt-C59, both other Wnt inhibitors did not result in a successful generation of cardiomyocytes. The different efficacy of the tested Wnt inhibitors to differentiate pluripotent stem cells into cardiomyocytes suggests that the specific inhibition of the Wnt pathway by blocking Wnt secretion seems to be a key mechanism.

In one embodiment, step c) comprises incubating the cells for 24-72 hours, preferably for 48 hours in an insulin-free medium comprising Wnt-C59.

In one embodiment, the insulin-free medium of step b) and c) is a serum-free medium. In one embodiment, the insulin-free medium is RPMI 1680 (Gibco).

In one embodiment, the cells are incubated in an insulin-free medium for 24 hours to 48 hours, preferably 48 hours between each step b) and c). In one embodiment, the medium is a serum-free medium. In another embodiment, the medium comprises ascorbic acid.

In one embodiment, the cells are incubated in a serum-free, insulin-free medium comprising ascorbic acid for 24 hours to 48 hours, preferably 48 hours between each step, b) and c).

In one embodiment, the method for differentiation of pluripotent cells into cardiomyocytes as described by any one of the embodiments above additionally comprises step d) incubating the cells in medium comprising insulin. At this later stage, insulin promotes proliferation of cardiomyocytes and their cardiac precursor cells.

In one embodiment, step d) comprises incubating the cells for 36-60 hours, preferably for 48 hours in medium comprising insulin. In one embodiment, the medium is a serum-free medium. In another embodiment, the medium comprises ascorbic acid.

Suitable media to be used in the expansion step d) are, for example, DMEM, high glucose+L-glutamine+pyruvate and carnitine, taurine, creatine, BSA, vitamin C or iCell Cardiomyocytes Maintenance Medium from Cellular Dynamics International.

Preferably the media are changed in between each step, e.g., the medium is removed e.g., by aspiration or centrifuging the cells and discarding the supernatant and then the medium used in the subsequent step is added to the cells. In one embodiment the cells are washed with a suitable buffer or medium prior to adding the medium of the subsequent step to remove any dead cells. Buffers or media useful for washing the cells are known in the art. One example of a suitable buffer for washing the cells is e.g., phosphate buffered saline (PBS).

In one embodiment, the pluripotent cells useful in the method for differentiation are cultivated under conditions permitting stable growth and/or duplication times. For example, the cells are grown in pluripotency medium and passaged several times. "Pluripotency medium" as used herein refers to any chemically defined medium useful for the attachment of the pluripotent stem cells as single cells on a monolayer while maintaining their pluripotency and are well known in the art. In one embodiment, the pluripotency medium is a serum free medium comprising a small molecule inhibitor of the Rho-associated coiled-coil forming protein serine/threonine kinase (ROCK) family of protein kinases (herein referred to as ROCK kinase inhibitor).

In one embodiment, the ROCK kinase inhibitor is selected from the group of 1-(5-Isoquinolinesulfonyl)homopiperazine), N-Benzyl-2-(pyrimidin-4-ylamino) thiazole-4-carboxamide) and (+)-(R)-trans-4-(1-aminoethyl)-N-(4-pyridyl)cyclo-hexanecarboxamide dihydrochloride.

Examples of ROCK kinase inhibitor useful herein are Fasudil (1-(5-Isoquinolinesulfonyl)homopiperazine), Thiazovivin (N-Benzyl-2-(pyrimidin-4-10 ylamino)thiazole-4-carboxamide) and Y27632 ((+)-(R)-trans-4-(1-aminoethyl)-N-(4-pyridyl)cyclo-hexanecarboxamide dihydrochloride, e.g. Catalogue Number: 1254 from Tocris bioscience). In one preferred embodiment, the ROCK kinase inhibitor is Y27632. In one embodiment, the pluripotency medium is a serum-free medium comprising 2-20 µM Y27632, preferably 5-10 µM Y27632. In another embodiment, the pluripotency medium is a serum-free medium comprising 2-20 µM Fasudil. In another embodiment, the pluripotency medium is a serum-free medium comprising 0.2-10 µM Thiazovivin.

With the new method presented herein it is now possible to differentiate cardiomyocytes expressing alpha actinin and troponin T from pluripotent stem cells with a yield of up to 60-98%.

In one embodiment, the method further comprises step e) replating the cells and incubating them in insulin-free medium. This step further increases the purity of the cardiomyocytes. In one embodiment, the cells are replated and incubated in insulin-free medium supplemented with fetal bovine serum for 18-32 hours, preferably for 24 hours. In one such embodiment, the medium further comprises a ROCK inhibitor. In one embodiment, the ROCK inhibitor is Y-27632.

The cardiomyocytes obtained by the method described herein can be expanded for several passages and retain their functional properties after freezing and thawing.

As used herein the term "differentiating", "differentiation" refers to one or more steps to convert a less-differentiated cell into a somatic cell, for example to convert a pluripotent stem cell into a cardiomyocyte. Differentiation of a pluripotent stem cell to cardiomyocytes is achieved by the method described herein.

The term "stem cell" as used herein refers to a cell that has the ability for self-renewal. An "undifferentiated stem cell" as used herein refers to a stem cell that has the ability to differentiate into a diverse range of cell types. As used herein, "pluripotent stem cells" refers to a stem cell that can give rise to cells of multiple cell types. Pluripotent stem cells (PSCs) include human embryonic stem cells (hESCs) and human induced pluripotent stem cells (hiPSCs). Human induced pluripotent stem cells can be derived from reprogrammed somatic cells, e.g. by transduction of four defined factors (Sox2, Oct4, Klf4, c-Myc) by methods known in the art. The human somatic cells can be obtained from a healthy individual or from a patient. These donor cells can be easily obtained from any suitable source. Preferred herein are sources that allow isolation of donor cells without invasive procedures on the human body, for example human skin cells, blood cells or cells obtainable from urine samples. Although human pluripotent stem cells are preferred, the method is also applicable to non-human pluripotent stem cells, such as primate, rodent (e.g., rat, mouse, rabbit) and dog pluripotent stem cells.

As used herein, "cardiomyocytes" are cells that express at least the cellular marker troponin T (troponin T Type 2 (Cardiac), gene symbol TNNT2, Entrez Gene: 7139, UniProtKB: P45379), and in a preferred embodiment also the cellular marker alpha actinin (ACTN2 actinin, alpha 2, gene symbol ACTN2, Entrez Gene: 88, UniProtKB: P35609). Expression of troponin T and/or alpha actinin can be assessed by methods known in the art, for example by FACS analysis as described in the Example section below. Cardiomyocytes can express spontaneous periodic contractile activity ("beating"). This means that when the cardiomyocytes obtained by the method of the invention are cultured in a suitable tissue culture environment with an appropriate Ca++ concentration and electrolyte balance, the cells can be observed to contract in a periodic fashion across one axis of the cell, and then release from contraction, without having to add any additional components to the culture medium. In addition, the cells obtained by the method disclosed herein can express other characteristics of cardiomyocytes, such as ion channel or appropriate electrophysiology.

As used herein, "proliferating cardiomyocytes" are cells that express expressing alpha actinin and troponin T and which proliferate by cell division.

"Expression of marker" means that a certain gene is transcribed into mRNA and usually is subsequently translated into a protein (its gene product) which exerts a certain function in a cell. The expression of a marker can be detected and quantified on the RNA level or on the protein level by methods known in the art. Preferred herein is the detection of the expression of a marker on the protein level, e.g., by testing for the presence of a certain protein with antibodies binding to the marker.

Any one of the above embodiments may be present singly or in combination.

In one embodiment of the present invention, a method for generating patient specific or healthy individual specific cardiomyocytes is provided. Towards this end, human induced pluripotent stem cells (iPSCs) obtained from a patient or healthy individual are differentiated into cardiomyocytes using the method described herein. The patient-specific human iPSCs can be obtained by methods known in the art by reprogramming somatic cells obtained from the patients or healthy individuals to pluripotent stem cells. For example, fibroblast cells, keratinocytes or adipocytes may be obtained by skin biopsy from the individual in need of treatment or from a healthy individual and reprogrammed to induced pluripotent stem cells by the methods known in the art. Other somatic cells suitable as a source for induced pluripotent stem cells are leucocytes cells obtained from blood samples or epithelial cells or other cells obtained from urine samples. The patient specific induced pluripotent stem cells are then differentiated to patient specific or healthy individual specific cardiomyocytes by the method described herein. In another aspect of the invention, a population of cardiomyocytes produced by any of the foregoing methods is provided. Preferably, the population of cardiomyocytes is patient specific, i.e., derived from iPSCs obtained from diseased individuals. In another embodiment the population of cardiomyocytes is obtained from a healthy individual.

Patient derived cardiomyocytes represent a disease-relevant in vitro model to study the pathophysiology of various diseases, such as dilated cardiomyopathy, hypertrophic cardiomyopathy, restrictive cardiomyopathy, arrhythmogenic right ventricular cardiomyopathy, coronary heart disease, etc. In one embodiment the cardiomyocytes obtained by this method are used for screening for compounds that reverse, inhibit, or prevent diseases caused by dysfunction of heart cells, e.g., cardiac hypertrophy, decreased beating efficiency, disorganized striation of the cardiomyocyte, insufficient calcium handling. Preferably, the cardiomyocytes obtained by the method of the invention described herein are derived from diseased subjects. In another embodiment, the cardiomyocytes obtained by this method are used for screening and evaluating new targets and compounds for treatment of heart diseases, e.g., those mentioned above. Preferably, the cardiomyocytes obtained by the method of the invention described herein are derived from individuals affected by diseases such as, for example, dilated cardiomyopathy, hypertrophic cardiomyopathy, restrictive cardiomyopathy, arrhythmogenic right ventricular cardiomyopathy, and coronary heart disease. Differentiating cardiomyocytes from diseased subjects represents a unique opportunity to early evaluate drug safety in a human background paradigm. In another embodiment, the cardiomyocytes obtained by this method are used as an in vitro model of the heart.

The present invention provides a highly efficient method to supply patient specific cardiomyocytes or compatible cells from healthy individuals with the same HLA type suitable for transplantation, both derived in xeno-free conditions. "Xeno-free culture conditions" refers to a medium and a substrate for attachment that comprising components only of human and recombinant origin. Thus the risk of contamination with xenopathogens is circumvented and the renal cells are safe for use in regenerative medicine. Differentiation of patient specific induced pluripotent stem cells (iPSCs) into patient specific cardiomyocytes with the method described herein represents an easy accessible and reproducible technology to generate autologous sources of cardiomyocytes. The use of autologous and/or compatible cells in cell therapy offers a major advantage over the use of non-autologous cells, which are likely to be subject to immunological rejection. In contrast, autologous cells are unlikely to elicit significant immunological responses.

In a further preferred aspect of the invention, the generation of a BioBank of patient-specific cardiomyocytes is envisaged. In one embodiment, a BioBank comprising different populations of cardiomyocytes obtained from healthy individuals and/or patients is generated. The term "BioBank" as used herein means a library of biological samples taken from different individuals or species. The archived collection of specimen and associated data is intended for research purposes with the aim of addressing diseases associated with, for example, dilated cardiomyopathy, hypertrophic cardiomyopathy, restrictive cardiomyopathy, arrhythmogenic right ventricular cardiomyopathy, and coronary heart disease. In another embodiment, the BioBank is used for vascular regenerative medicine approaches.

In another aspect, the invention provides a therapeutic composition comprising cardiomyocytes produced by any one of the foregoing methods or comprising any one of the foregoing cell populations. Preferably, the therapeutic compositions further comprise a physiologically compatible solution including, for example, a phosphate-buffered saline with 5% human serum albumin. The therapeutic composition can be used to treat, prevent, or stabilize diseases such as, for example, dilated cardiomyopathy, hypertrophic cardiomyopathy, restrictive cardiomyopathy, arrhythmogenic right ventricular cardiomyopathy, and coronary heart disease. For example, fibroblast cells, keratinocytes, or adipocytes may be obtained by skin biopsy from the individual in need of treatment or from a healthy individual, and reprogrammed to induced pluripotent stem cells by the methods known in the art. (See, e.g., Takahashi et al., (2007) Cell 131:861-872.) Other somatic cells suitable as a source for induced pluripotent stem cells are leucocytes cells obtained from blood samples or epithelial cells or other cells obtained from urine samples. The patient-specific induced pluripotent stem cells are then differentiated to cardiomyocytes by the method described herein, harvested, and introduced into the individual to treat the condition. The cardiomyocytes produced by the method of the present invention may be used to replace or assist the normal function of diseased or damaged tissue.

Another embodiment of the invention is the use of BioBanks of cardiomyocytes for therapy of diseases associated with dilated cardiomyopathy, hypertrophic cardiomyopathy, restrictive cardiomyopathy, arrhythmogenic right ventricular cardiomyopathy, and coronary heart disease. The BioBanks preferably comprise cardiomyocytes obtained from patients or healthy individuals with several HLA types. Transplanting cells obtained from a healthy donor to an individual in need of treatment with a compatible HLA type obviates the significant problem of rejection reactions normally associated with heterologous cell transplants. Conventionally, rejection is prevented or reduced by the administration of immunosuppressants or anti-rejection drugs such as cyclosporine. However, such drugs have significant adverse side-effects, e.g., immunosuppression, carcinogenic properties, kidney toxicity as well as being very expensive. The present invention eliminates, or at least significantly reduces, the need for anti-rejection drugs, such as cyclosporine, imulan, FK-506, glucocorticoids, and rapamycin, and derivatives thereof.

With respect to the therapeutic methods of the invention, it is not intended that the administration of cardiomyocytes to a mammal be limited to a particular mode of administration, dosage, or frequency of dosing; the present invention contemplates all modes of administration, including intramuscular, intravenous, intrarticular, intralesional, subcutaneous, or any other route sufficient to provide a dose adequate to prevent or treat a disease. The cardiomyocytes may be administered to the mammal in a single dose or multiple doses. When multiple doses are administered, the doses may be separated from one another by, for example, one week, one month, one year, or ten years. One or more growth factors, hormones, interleukins, cytokines, small molecules or other cells may also be administered before, during, or after administration of the cells to further bias them towards a particular cell type.

EXAMPLES

Materials and Methods

CP21R7: 3-(3-Amino-phenyl)-4-(1-methyl-1H-indol-3-yl)-pyrrole-2,5-dione (also referred to as "compound 21" or "CP21" herein; (See e.g., Gong et al. (2010) Bioorganic& Medicinal Chemistry Letters 20:1693-1696.):

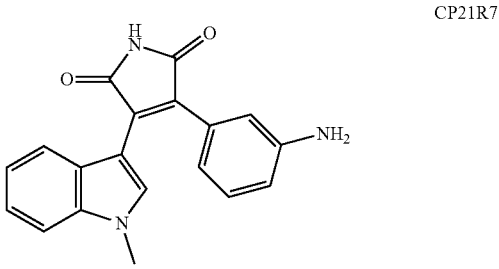 [SMILES: Cn1cc(C2=C(c3cccc(N)c3)C(=O)NC2=O)c2ccccc21]

Wnt-C59: 2-(4-(2-methylpyridin-4-yl)phenyl)-N-(4-(pyridin-3-yl)phenyl)acetamide (Cellagen Technology, Cat. C7641-2s; International Patent Application Publication No. WO 2010 101849):

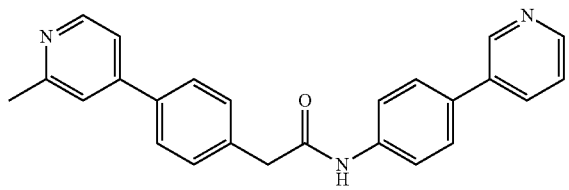 [SMILES: Cc1cc(-c2ccc(CC(=O)Nc3ccc(-c4cccnc4)cc3)cc2)ccn1]

Human ESCs: SA001, LOT CA001 were isolated on Mar. 20, 2001 at Göteborg University and Cellartis AB Arvid Wallgrens Backe 20, SE-413 46 Göteborg, SWEDEN follows all applicable laws in Sweden and is approved by the Local Research Ethics Committees at Göteborg University and Uppsala University. Embryo source: Frozen, surplus from IVF. Donor confidentiality: In order to protect the privacy and the confidentiality of the donors, all identifiers associated with the embryo donors have been removed. Thus, no information about the donors is accessible. Notably, the donation did not result in any financial gain for the donors. We have the approval to work with hESCs and to derive different cell lines. The responsible ethical committee (Ethikkommission beider Basel) and the Federal office of public health have approved our research project. (Ref-No: R-FP-S-1-0002-0000).

Human iPSCs: Catalogue Number: SC101A-1 Lot. Number: 110218-FF from SBI System Biosciences/Catalogue Number: A13777 from Life technologies Gibco® Episomal hiPSC Line.

Human pluripotent stem cells are routinely cultured on hESC-qualified Matrigel (BD Bioscience) in TeSR1 medium (Stem cell Technologies). Cultures are passaged every 4-6 days using StemPro Accutase (Invitrogen). For an increased viability TeSR1 medium is comprising 10 µM ROCK-inhibitor one hour prior enzymatic dissociation.

| 500 ml Differentiation medium | | |
|---|---|---|
| RPMI 1680 + Glutamax | 481 ml | GIBCO#61870 |
| Ascorbic Acid (10 mg/ml) (final concentration: 80 µg/ml) | 4 ml | Sigma#A4544 |
| B27 − Insulin (50x) | 10 ml | Invitrogen#05-0129SA |
| PenStrep (final concentration: 50 U/ml) | 5 ml | GIBCO#15140-122 |

| 500 ml Expansion medium | | |
|---|---|---|
| RPMI 1680 + Glutamax | 481 ml | GIBCO#61870 |
| Ascorbic Acid (10 mg/ml) (final concentration: 80 µg/ml) | 4 ml | Sigma#A4544 |
| B27 + Insulin (50x) | 10 ml | Invitrogen#12587-01 |
| PenStrep (final concentration: 50 U/ml) | 5 ml | GIBCO#15140-122 |

Further reagents and materials useful herein:
Matrigel (BD Bioscience, Cat. 354277)
mTeSR1 medium (Stemcell Technologies, Cat. 05850)
Accutase (Innovative Cell Technologies, Cat. AT-104)
Rock inhibitor, Y-27632 (Millipore, Cat. SCM075)
RPMI medium (Gibco by Life Technologies, Cat. 61870)
Ascorbic Acid (Sigma, Cat. A4544)
50xB-27® Supplement Minus Insulin (Gibco by Life Technologies, Cat. 0050129SA)
Penicillin-Streptomycin (Gibco by Life Technologies, Cat. 15070)
50xB27 plus Insulin, minus Vitamin A (Gibco by Life Technologies, Cat. 12587)
0.05% Trypsin/EDTA, 1× (Gibco by Life Technologies, Cat. 25300)
autoMACS Running Buffer (Miltenyi, Cat. 130-091-221)
Inside Perm+InsideFix (Miltenyi, Inside Stain Kit, Cat. 130-090-477)
0.1% Gelatine (Millipore, Cat. ES-006-B)
Cryogenic vial (Corning#430659)
Mr. Frosty Freezing Container (Thermo Scientific#5100-0001)
DMSO (Sigma#D2438)
Fetal Bovine Serum (Invitrogen#16000044)
Falcon Cell Culture Dishes 35×10 mm (BD#353001)
Falcon Cell Culture Dishes 100×20 mm (BD#353003)
6-well-plates Corning Costar (Sigma#CLS3516)
Anti-Sarcomeric Alpha Actinin [EA-53] antibody (Abcam, Cat. ab9465)
Anti-Cardiac Troponin T antibody (Abcam, Cat. ab45932)
Alexa Fluor® 488 and Donkey Anti-Mouse IgG (H+L) (Invitrogen, Cat. A21202)
Alexa Fluor® 647 Donkey Anti-Rabbit IgG (H+L) (Invitrogen, Cat. A31573)
Alexa Fluor® 555 Donkey Anti-Rabbit IgG (H+L) (Invitrogen, Cat. A31572)
Hoechst 33258, Pentahydrate (bis-Benzimide) (Molecular Probes, Cat. H3569)

Example 1. Differentiation of Cardiomyocytes from Human Embryonic Stem Cells (hESC) and Induced Pluripotent Stem Cells (iPSC)

Human embryonic stem cells (hESC) or induced pluripotent stem cells (iPSC) were cultured in 56 cm$^2$ dishes coated with Matrigel (BD Bioscience, Cat. 354277) at 37° C. and 5% $CO_2$ in 10 ml mTeSR1 medium (Stemcell Technologies, Cat. 05850).

Before starting the cardiomyocyte differentiation, the cells were passaged 3-4 times to ensure that the pluripotent stem cells showed stable growth and duplication times.

To propagate pluripotent stem cells by conserving their pluripotent state, hESC or iPSC were treated with the following: the cells were washed once with 10 ml PBS−/−, and afterwards incubated with 3 ml Accutase (Innovative Cell Technologies, Cat. AT-104) for 2-3 minutes at 37° C. and 5% $CO_2$, to detach the cells.

The enzymatic reaction of Accutase was stopped with 7 ml mTeSR1 and followed by centrifugation of the cells for 3 minutes at 500×g.

The cells were resuspended in 10 ml mTeSR1, and counted. For further cultivation, 2×10$^6$ cells were plate on 56 cm$^2$ dishes with fresh coated Matrigel. Further the hESC or iPSC were cultivated in 10 ml mTeSR1 and 10 µM Rock inhibitor, Y-27632 (Millipore, Cat. SCM075) at 37° C. and 5% $CO_2$. Subsequently, 10 ml mTeSR1 medium was changed daily and the pluripotent stem cells were cultivated to a density of 80% before passaging.

For successful differentiation into cardiomyocytes, pluripotent stem cells were plated at high density using 5.5×10$^5$/cm$^2$ of hESC or iPSC. Passaging and cultivation were performed as described above for pluripotent stem cells.

After 24 hours (day 1) the hESC or iPSC were washed once with 180 µl/cm$^2$ PBS−/− and the cultivation medium was changed to 180 µl/cm$^2$ differentiation medium.

To initiate the differentiation of the pluripotent stem cells towards the cardiac lineage, the medium comprised 2 µM compound 21 (CP21,) a small molecule and highly selective inhibitor of glycogen synthase kinase 3 (GSK3β).

After 24 hours (day 2) incubation with CP21, the cells were washed with PBS−/− as described above and cultivated for 48 hours in 220 µl/cm$^2$ differentiation medium.

After 48 hours (day 4), the cells were washed with PBS−/− as described above and cultivated for 48 hours in 220 µl/cm$^2$ differentiation medium comprising 2 µM Wnt-C59 (Cellagen Technology, Cat. C7641-2s, International Patent Application Publication No. WO 20101 01849), a potent Wnt signaling inhibitor, by blocking Wnt secretion.

After 48 hours (day 6), the cells were washed with PBS−/− as described above and cultivated for 48 hours in in 220 µl/cm$^2$ differentiation medium.

After 48 hours (day 8), the cells were washed with PBS−/− as described above and cultivated for 48 hours in 220 µl/cm$^2$ RPMI medium comprising ascorbic acid, penicillin-streptomycin, but now including B27 plus insulin, minus vitamin A (=expansion medium)

First cardiomyocytes visible by beating cells were observed at day 8 of differentiation further increasing until day 14.

Subsequent medium changes were performed every 48 hours using 220 µl/cm$^2$ expansion medium.

Example 2. Cell Characterization

To test the efficiency of the differentiation process, the cardiomyocytes were characterized at differentiation day 14 by cell immunohistochemistry and Fluorescence Activated Cell Sorting (FACS) using antigens specific to cardiomyocytes.

Fluorescence Activated Cell Sorting (FACS) Analysis

Cells were washed with 180 µl/cm² PBS−/− and dissociated 5-10 minutes with 100 µl/cm² 0.05% 1× Trypsin/EDTA (Gibco by Life Technologies, Cat. 25300) at 37° C. and 5% $CO_2$.

If necessary, the cells were gently scraped from the cultivation vessel, pipetted up and down, and subsequently incubated 5-10 minutes at 37° C. and 5% $CO_2$.

Afterwards threefold expansion medium and 10% fetal bovine serum (FBS) was added.

Then, the cells were filtered through 100 µm cell strainer and counted.

For analysis, $1 \times 10^6$ cells in suspension were transferred into 1.5 ml tube. After 3 minutes centrifugation at 500×g, supernatant was removed and cells were fixed with 50 µl of Inside Fix (Miltenyi, Inside Stain Kit, Cat. 130-090-477) and 50 µl PBS−/− for 15 minutes at room temperature in the dark.

Afterwards, 100 µl autoMACS Running Buffer (Miltenyi, Cat. 130-091-221) was added and the cell suspension centrifuged. Supernatant was removed and cells were washed with 100 µl Inside Perm (Miltenyi, Inside Stain Kit, Cat. 130-090-477), centrifuged and supernatant was removed. Cells were incubated with Anti-Sarcomeric Alpha Actinin [EA-53] antibody (Abcam, Cat.ab9465) and Anti-Cardiac Troponin T antibody (Abcam, Cat.ab45932), 1:100 diluted in Inside Perm for 1 hour at 4° C.

Afterwards, cells were washed with 500 µl Running Buffer, centrifuged, and the supernatant was removed. Cells were incubated with secondary antibodies (1:1000 in Inside Perm) for 10 minutes at room temperature. The following secondary antibodies were used: Alexa Fluor® 488 Donkey Anti-Mouse IgG (H+L) (Invitrogen, Cat.A21202) and Alexa Fluor® 647 Donkey Anti-Rabbit IgG (H+L) (Invitrogen, Cat.A31573).

Subsequently, cells were washed with 500 µl Running Buffer, after centrifugation resuspended cells in 500 µl Running Buffer and measured by fluorescence activated cell sorting (FACS) system.

Example 3. Differentiation of Cardiomyocytes from Human Embryonic Stem Cells (hESC) and Induced Pluripotent Stem Cells (iPSC) Using Different CP21 Concentrations The protocol as described above was repeated with different CP21 concentrations. The results are shown in Table 1 below: (−) No cardiomyocytes obtained, (+)—(+++): Amount of cardiomyocytes obtained.

TABLE 1

| Cp21 conc. in µM | 0 | 0.3 | 1 | 2 | 3 | 5 | 10 |
|---|---|---|---|---|---|---|---|
| Experiment I | − | − | + | ++ | ++ | + | − |
| Experiment II | − | − | + | +++ | + | − | − |
| Experiment III | − | − | + | ++ | ++ | − | − |

Example 4. Purification

To increase purity of the cardiomyocytes an enrichment step was developed.

As described above cells were washed with 180 µl/cm² PBS−/− and dissociated 5-10 minutes with 100 µl/cm² 0.05% 1× Trypsin/EDTA (Gibco by Life Technologies, Cat.25300) at 37° C. and 5% $CO_2$.

If necessary, the cells were gently scraped from the cultivation vessel, pipetted up and down and subsequently incubated 5-10 minutes at 37° C. and 5% $CO_2$.

Afterwards threefold expansion medium and 10% fetal bovine serum (FBS) was added.

Then, cells were filtered through 100 µm cell strainer and counted.

Fresh plates coated with 130 µl/cm² 0.1% Gelatine (Millipore, Cat.ES-006-B) were incubated for 1 hour at 37° C. $2.7 \times 10^5$/cm² cells were plated in 180 µl/cm² expansion medium 10% fetal bovine serum (FBS). In addition 10 µM Rock inhibitor was added. After 24 hours 220 µl/cm² medium was changed expansion medium without FBS and Rock inhibitor. The medium was changed every 48 hours.

At day 18-21 cells were analyzed with FACS and again replated as described above in different formats for following analysis: Immunoflourescence stainings, xCELLigence to detect Beating Rhythm and Proarrhythmic Effects of Compounds in Stem Cell-Derived Cardiomyocytes.

Cells were transferred to plate formats compliant with assay conditions. Cells were allowed to attach for 24 hours in 200 µl/cm² expansion medium plus 10% fetal bovine serum (FBS). In addition 10 µM Rock inhibitor was added. After 24 hours 220 µl/cm² expansion medium was changed without FBS and Rock inhibitor. The medium was changed every 48 hours.

Example 5. Freezing and Thawing of Cardiomyocytes

At day 14 cardiomyocytes were replated as described above for the purification method. On day 18, cells were dissociated as outlined above and subsequently analyzed by FACS for their alpha-actinin and troponin T expression. Cultures with 80% and above cardiomyocytes were subjected to the freezing protocol. Culture with less than 80% cardiomyocytes were discarded.

Cells were counted and $4 \times 10^6$ cells were frozen with 1 ml of cooled FBS comprising 10% DMSO and 10 µM Y-27632 per cryogenic vial.

Cells were centrifuged for 3 minutes at 500×g and subsequently resuspended carefully in FBS supplemented 10% DMSO and 10 µM Y-27632. 1 ml aliquots of the cardiomyocytes cell suspensions were filled into 4° C. pre-chilled cryogenic vials and frozen for 24 hours at −80° C. Afterwards, cryovials were stored in liquid nitrogen.

To thaw the cardiomyocytes, a vial was incubated for 1-2 minutes at 37° C. in a water bath and the cells were carefully transferred in 10 ml expansion medium plus 10% fetal bovine serum. Cells were centrifuged for 2 minutes at 300×g. Afterwards the pellet was resuspended in 6 ml expansion medium plus 10% fetal bovine serum and 10 µM Y-27632 and plated onto 3 wells of 6-well plate coated with 0.1% gelatin. After 24 hours, the cells were changed to 220 µl/cm² expansion medium without FBS and Y-27632. Subsequently, the medium was changed every 3 days, and after 5-7 days the cells were plated onto plate formats compliant with assay conditions (e.g. Assay for detecting disorganization of cardiac striation: 96 well format; Assay for recording beating frequency: 96 well format).

Example 6. xCELLigent Cardiomyocyte Beating Analysis

Isoproterenol increases the heart rate and myocardial contractility by stimulating cardiac beta-1 receptors. To detect this proarrhythmic effect in the stem cell derived cardiomyocytes, $7 \times 10^4/cm^2$ cells were plated on special E-Plate Cardio 96 (Roche, Cat. No. 05232368001) coated with 130 µl/cm² 0.1% Gelatine for 1 hour at 37° C. After cells attached to the plate and recovered for 2 days as described above, medium was changed to iCell Cardiomyocytes Maintenance Medium (Cellular Dynamics, Cat. No.CMM-100-120-005). Cells were measured using the xCELLigence RTCA Cardio System (Roche Applied Science). 7 days after plating the cells were treated with 3 µM Isoproterenol and measured directly. Each 96-well plate was measured at a resolution of 12.9 ms. The first 3 minutes were measured without interruption and over the next 24 hours the cells were measured every 15 minutes for 1 minute duration.

Example 7. Immunofluorescence Staining

For immunofluorescence staining, cells were fixed with 4% Paraformaldehyd for 15 minutes at room temperature. After washing cells with PBS−/−, the cells were blocked and permeabilized for 20 minutes at room temperature with 10% donkey serum in PBS−/− and 0.1% Triton (Blocking Buffer). Afterwards the cells were stained overnight in blocking buffer at 4° C. with 1:100 diluted primary antibodies Anti-Sarcomeric Alpha Actinin [EA-53] antibody (Abcam, Cat.ab9465) and Anti-Cardiac Troponin T antibody (Abcam, Cat.ab45932).

Cells were washed with PBS−/− and stained 1:1000 in blocking buffer with secondary antibodies Alexa Fluor® 488 and Donkey Anti-Mouse IgG (H+L) (Invitrogen, Cat.A21202) and Alexa Fluor® 555 Donkey Anti-Rabbit IgG (H+L) (Invitrogen, Cat.A31572) for one hour at room temperature in blocking buffer. Nuclei were stained after several PBS−/− washing steps with 1:1000 diluted Hoechst 33258, Pentahydrate (bis-Benzimide) (Molecular Probes, Cat.H3569) in PBS−/−.

Results

After differentiation, the cells were analyzed for their cardiomyocyte content. FIG. 1 depicts a FACS analysis quantifying cardiomyocytes on differentiation day 14.

An average of 80-90% cardiomyocytes characterized by alpha actinin and troponin T double positive cells was obtained. As shown in FIG. 1, a subpopulation of the cells stained single positive for alpha actinin (5-10%). This is an indication of more immature cardiomyocytes and for this reason this population was not included for scoring. This result was independent of using hESC (FIG. 1A) or iPSC (FIG. 1B) as a source of pluripotent stem cells. Starting with $5.5 \times 10^5/cm^2$ pluripotent stem cells the differentiation protocol generated an average of $4-5 \times 10^5/cm^2$ alpha actinin and troponin T positive cardiomyocytes.

To demonstrate robustness of the differentiation protocol we performed several experiments and analyzed the content of cardiomyocytes in each culture. FIG. 2 depicts 10 independent experiments showing differentiation efficacies towards cardiomyocytes ranging between 95% and 40%. However, the majority of the experiments (7 out of 10) showed a cardiomyocyte content over 75%, which is an acceptable ratio. Experiments generating 60% cardiomyocytes and more were progressed. Differentiations with less than 60% cardiomyocytes were discarded. The variability between experiments is most likely caused by the quality and cultivation state of the pluripotent stem cells at the beginning of the differentiation.

To further increase purity towards cardiomyocytes, an additional purification step was established. At differentiation day 14, the cells were detached and analysed by FACS. FIG. 3A shows that the culture counts $9 \times 10^5/cm^2$ cells containing 60% ($5.4 \times 10^5/cm^2$) cardiomyocytes at day 14. For the purification method to be successful, the minimum percentage of alpha actinin positive cells should be 60% and more. The dissociated cells are replated ($2.7 \times 10^5/cm^2$) and cultivated in expansion medium. After 7 days cells were harvested, $4.5 \times 10^5/cm^2$ cells were counted and analyzed. FIG. 3B shows that after the purification step, the cardiomyocyte content in the culture increases from 60% to 98%, demonstrating the efficient generation of $4.4 \times 10^5/cm^2$ highly enriched cardiomyocytes by using this method. Afterwards, cells were transferred to cultivation formats compliant with assay conditions.

The cardiomyocytes were analyzed by immunofluorescence for further characterization. FIG. 4 shows an immunofluorescence stain of cardiomyocytes at day 27 using antibodies against alpha actinin (green*), troponin T (red#), and the nuclei specific Hoechst stain (blue+). The resulting immunofluorescence in FIG. 4 shows cells with alpha actinin and troponin T specific striation that is characteristic for cardiomyocytes.

Activation of β-receptors on the heart induces positive chronotropic effects in cardiomyocytes. To confirm that the pluripotent stem cell derived cardiomyocytes respond to β-receptor activation, the cardiomyocytes were incubated with the β-receptor agonist isoproterenol and subsequently analysed using the xCELLigence system. FIG. 5 shows that after incubating the pluripotent stem cell derived cardiomyocytes with 3 µM isoproterenol, the beating rate increased to 60 beats per minute from 45 beats per minute when compared to untreated control. This experiment further demonstrated that the pluripotent stem cell derived cardiomyocytes generated by this differentiation protocol resemble functional human cardiomyocytes.

Freezing and thawing of cardiomyocytes has been traditionally difficult due to the low level of cell recovery after thawing.

Since it is important for assay development to have large batches of identical cells, we tested if the pluripotent stem cell derived cardiomyocytes can be stored in a freezer and afterwards thawed. We tried to freeze the differentiated cardiomyocytes at different ages (day 14, 18 and 32). As can be seen in FIG. 6, cardiomyocytes frozen at earlier differentiation stages show a higher cell survival rate after thawing. However, cell thawed after purification on day 18 of differentiation provided the best conditions for using the cells for pharmaceutical assays. At this stage cells show a much higher purity after thawing and cardiomyocytes could be directly transferred onto cell culture vessels that are compliant with assay formats.

When thawing cardiomyocytes frozen at differentiation day 32, the survival rate was very low and many cells were lost. This is due to the low proliferation rate of the cells at this stage resulting in low recovery of cardiomyocytes after thawing.

We determined that the optimal time for freezing pluripotent derived cardiomyocytes was after purification at differentiation day 18. At this stage recovery rate is on average more than 85% alpha actinin and troponin T positive cells and cardiomyocytes are still proliferating providing optimal conditions for using the cells further for assay development.

What is claimed is:

1. A method for differentiating pluripotent stem cells into cardiomyocytes with high efficiency, the method comprising:

a) plating pluripotent stem cells at a density of $3-7\times10^5/cm^2$,
b) culturing the cells for 24 hours,
c) incubating the cells in an insulin-free medium for 24 hours, wherein the medium comprises 0.5-5 µM of the compound CP21 having the formula:

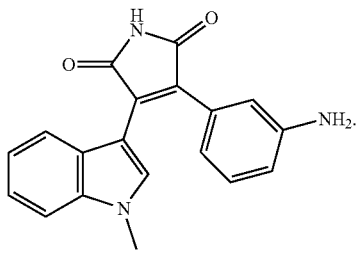 [SMILES: Cn1cc(C2=C(c3cccc(N)c3)C(=O)NC2=O)c2ccccc21]

3-(3-Amino-phenyl)-4-(1-methyl-1H-indol-3-yl)-pyrrole-2,5-dione,
d) washing the cells to remove the medium and incubating the cells in insulin-free media for 24-48 hours,
e) washing the cells to remove the medium and incubating the cells in insulin-free medium comprising 2 µM Wnt-059 for 24-48 hours,
f) washing the cells to remove the medium and incubating the cells for 48 hours in insulin-free differentiation medium, and
g) washing the cells to remove the differentiation medium and incubating the cells for 48 hours in expansion medium, wherein the expansion medium comprises insulin and does not comprise vitamin A,
wherein the time span from step c) to step g) is within 10 days and the yield of differentiated cardiomyocytes after step g) is over 75%.

2. The method of claim 1, wherein the cells in step a) are at a density of $5.5\times10^5/cm^2$.

3. The method of claim 1, wherein the insulin-free medium of step c) comprises 2 µM of the compound CP21.

4. The method of claim 1, wherein the insulin-free medium further comprises ascorbic acid.

5. The method of claim 1, wherein the pluripotent stem cell is an induced pluripotent stem cell.

6. The method of claim 5, wherein the induced pluripotent stem cell is a human induced pluripotent stem cell.

7. The method of claim 5, wherein the induced pluripotent stem cell is obtained from a subject suffering from a disease caused by dysfunction of heart cells.

* * * * *